Figure 1:
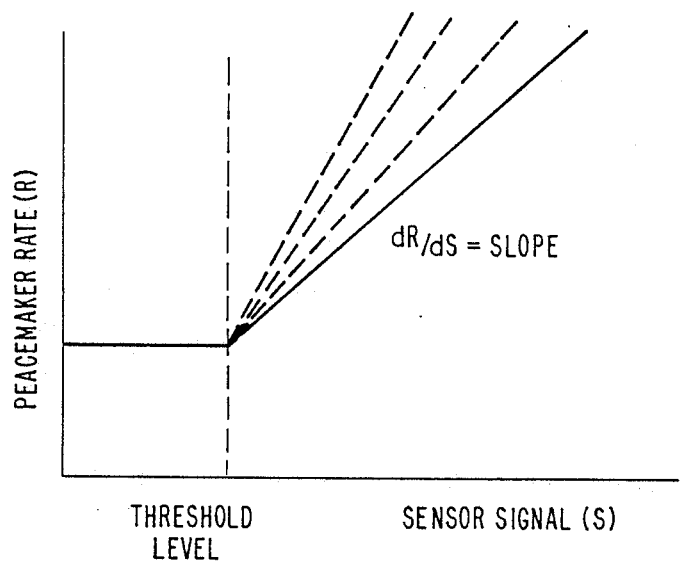

United States Patent [19]
Webb et al.

[11] Patent Number: 4,966,146
[45] Date of Patent: Oct. 30, 1990

[54] RATE-RESPONSIVE PACEMAKER

[76] Inventors: Stuart C. Webb, 5 Lingholm Way, Barnet; Leland M. Lewis, 43 Prince George Avenue, Oakwood, London; Jayne A. Morris-Thurgood, 20 Pym Walk, Thame, Oxfordshire, all of United Kingdom

[21] Appl. No.: 295,936

[22] Filed: Jan. 11, 1989

[30] Foreign Application Priority Data

Jan. 14, 1988 [GB] United Kingdom ............... 8800810

[51] Int. Cl.⁵ .................................. A61N 1/36
[52] U.S. Cl. ................................... 128/419 PG
[58] Field of Search ............... 128/419 PG, 419 PT, 128/419 P, 903

[56] References Cited

U.S. PATENT DOCUMENTS

| | | | |
|---|---|---|---|
| 4,273,132 | 6/1981 | Hartlaub et al. | 128/419 PG |
| 4,340,062 | 7/1982 | Thompson et al. | 128/419 PG |
| 4,365,633 | 12/1982 | Loughmann et al. | 128/419 PG |
| 4,543,954 | 10/1985 | Cook et al. | 128/419 PG |
| 4,550,732 | 11/1985 | Batty, Jr. et al. | 128/419 PG |
| 4,562,840 | 1/1986 | Batina et al. | 128/903 |
| 4,596,251 | 6/1986 | Plicchi et al. | 128/419 PG |
| 4,719,920 | 1/1988 | Alt et al. | 128/419 PG |
| 4,721,110 | 1/1988 | Lampadius | 128/419 PG |
| 4,722,342 | 2/1988 | Amundson | 128/419 PG |
| 4,763,655 | 8/1988 | Wirtzfeld et al. | 128/419 PG |
| 4,771,780 | 9/1988 | Sholder | 128/419 PG |
| 4,782,836 | 11/1988 | Alt | 128/419 PG |
| 4,807,629 | 2/1989 | Baudino et al. | 128/419 PG |
| 4,817,606 | 4/1989 | Lekholm | 128/419 PG |
| 4,823,797 | 4/1989 | Heinze et al. | 128/419 PG |

FOREIGN PATENT DOCUMENTS

| | | | |
|---|---|---|---|
| 0015779 | 9/1980 | European Pat. Off. | 128/419 PG |
| 0058603 | 8/1982 | European Pat. Off. | 128/419 PG |
| 0077844 | 5/1983 | European Pat. Off. | 128/419 PG |
| 0077845 | 5/1983 | European Pat. Off. | 128/419 PG |
| 0080348 | 6/1983 | European Pat. Off. | 128/419 PG |
| 0089014 | 9/1983 | European Pat. Off. | 128/419 PG |
| 0096464 | 12/1983 | European Pat. Off. | 128/419 Pg |
| 0107483 | 5/1984 | European Pat. Off. | 128/419 PG |
| 0114679 | 8/1984 | European Pat. Off. | 128/419 PG |
| 0140472 | 5/1985 | European Pat. Off. | 128/419 PG |
| 0160801 | 11/1985 | European Pat. Off. | 128/419 PG |

(List continued on next page.)

OTHER PUBLICATIONS

Experience With a Two Sensor Controlled Rate-Adaptive Pace Maker System, by H. Heuer et al., vol. 6, No. 2/86, Jun. 1986, pp. 64–67 (Eng. trans.).
Sensor Pacing, Research Leads . . . by Kenneth M. Anderson, Medical Electronics, Oct. 1986, pp. 89 to 93.
Present State and Future Trends . . . by M. Schaldach, Medical Progress Through Technology, vol. 13, 1987, pp. 85–102.
"Activitrax" Technical Manual–Models 8400/8402/8403.
Sensolog 703 Pulse Generator–Physician's Manual.
Temperaturgesteurte Schrittmacherstimulation Erste Klinische Ergebnisse, by E. Alt, "Zeitschrift Fur Kardiologie", vol. 74, Settlement 5, Oct. 1985, p. 27.
Cardiac Pacemaker Regulated by Respiratory Rate and . . . by T. Segura et al., "Pace", vol. 11, Jul. 1988, pp. 1077–1084.

Primary Examiner—Francis Jaworski
Assistant Examiner—George Manuel
Attorney, Agent, or Firm—Frishauf, Holtz, Goodman & Woodward

[57] ABSTRACT

The slope and threshold of the rate responsive pacemaker are automatically adjustable to suit the physiological requirements of the user.

For threshold adjustment, the user performs a resting level of exertion and the sensor (3) signal is switched (14) to a threshold value generator (15) where its peak value is stored as the threshold value.

For slope adjustment, a target pacing rate is supplied to a store (17) by a programmer (13). The user performs a predetermined constant level of exertion. The resulting pacing rate is compared with the stored target rate in a comparator. The slope is adjusted (16) until the rates are equal. The value of slope is then stored (16).

The sensor (3) may sense any suitable biological variable.

15 Claims, 2 Drawing Sheets

FOREIGN PATENT DOCUMENTS

| | | | |
|---|---|---|---|
| 0178528 | 4/1986 | European Pat. Off. | 128/419 PG |
| 0191404 | 8/1986 | European Pat. Off. | 128/419 PG |
| 0201990 | 11/1986 | European Pat. Off. | 128/419 PG |
| 0216725 | 4/1987 | European Pat. Off. | 128/419 PG |
| 0222681 | 5/1987 | European Pat. Off. | 128/419 PG |
| 249818 | 12/1987 | European Pat. Off. | 128/419 PG |
| 0249820 | 12/1987 | European Pat. Off. | 128/419 PG |
| 0249821 | 12/1987 | European Pat. Off. | 128/419 PG |
| 0249824 | 12/1987 | European Pat. Off. | 128/419 PG |
| 0257116 | 3/1988 | European Pat. Off. | 128/419 PG |
| 0259658 | 3/1988 | European Pat. Off. | 128/419 PG |
| 3419439 | 11/1905 | Fed. Rep. of Germany | 128/419 PG |
| 81/01659 | 6/1981 | PCT Int'l Appl. | 128/419 PG |
| 87/01947 | 4/1987 | PCT Int'l Appl. | 128/419 PG |

RATE-RESPONSIVE PACEMAKER

The present invention relates to a cardiac pacemaker.

In the normal healthy individual the output of blood by the heart is varied continuously to meet the metabolic demands of the body The cardiac output changes with variations in the heart rate and the volume of blood pumped at each heart beat The cardiac output is the product of these two variables. During strenuous exercise a four or five fold increase in cardiac output may be required. Approximately 75% of this increase is achieved by elevation of the heart rate.

Patients with cardiac disease resulting in very slow heart rates frequently require treatment in the form of an implanted artificial pacemaker. This consists of a small electrical pulse generator that is connected to the heart by an insulated electrode lead usually positioned in the right ventricle.

Until recently the majority of such pacemakers were relatively simple devices that provided a constant frequency of stimulation. These suffer from the disadvantage that they are unable to increase the heart rate during exercise thereby limiting the degree of exertion that the patient is able to undertake This drawback has led to the development of two forms of pacemaker that can increase stimulation rate during exercise. The "ideal" system is a dual chamber pacemaker which has a second lead implanted in the right atrial chamber of the heart. This detects the rate of the heart's natural pacemaker and enables the artificial pacemaker to provide normal physiological changes in heart rate. However, such systems are not suitable for many patients and also have inherent technical and economic disadvantages.

An alternative approach that has been developed during recent years is the single chamber rate-responsive pacemaker. The fundamental principles of this device are as follows:

(A) A sensor is used to detect changes in a biological variable that are directly or indirectly proportional to the level of metabolic activity in the body. Evoked QT interval, respiratory rate, mixed venous temperature and body vibration are the main variables that are sensed by currently available rate-responsive pacemakers.

(B) The output from the sensor is processed by electronic circuitry to provide a signal that can be used to vary the stimulation rate provided by the pacemaker This circuitry is designed to perform a series of mathematical and logical functions that are known collectively as the rate-response algorithm.

The two principal functions are:

(i) To set the recognition level within the pacemaker for the amplitude of the sensor signal which must be exceeded in order for an increase in pacing rate to be initiated (threshold level).

(ii) To determine the precise mathematical relationship between changes in the sensor signal S and the change in pacing rate R to be provided by the pacemaker, (the slope dR/dS).

Conventional rate response algorithms incorporate a range of values for both the threshold and slope functions These values can be selected by telemetered instructions from an external programmer. The programmer is also used to select the minimum and maximum rates that the pacemaker will generate and to vary a number of other aspects of pacemaker function such as pulse amplitude and duration The objective of rate-responsive pacing is to provide changes in heart rate that are matched to the varying physiological requirements of individual patients. The conventional programming sequence required to attempt to attain such a match is as follows:

(1) Arbitrary selection of values for threshold and slope.

(2) Clinical evaluation of the resulting rate response Pacing rate must be monitored while the patient is performing different levels of exercise, e.g. at rest and during the performance of an exercise test.

(3) If an inappropriate response is detected, new values for the threshold and/or slope functions have to be selected and the clinical assessment undertaken again.

The latter two steps of the programming sequence may have to be repeated many times before an optimum rate-response is achieved This complex procedure is time consuming and therefore disadvantageous for both the patient and the medical staff involved.

According to an aspect of the present invention, there is provided a rate-responsive pacemaker which is selectively actuable to respond to a sensor signal representing an actual exercise level of a user to automatically adjust the rate-response algorithm in dependence on the sensor signal.

The sensor signal may be produced by any form of biological sensor.

An illustrative embodiment of the pacemaker has provision for adjusting two parameters of the rate-response algorithm. Those parameters are, for example, threshold and slope.

ADJUSTING THRESHOLD

The threshold setting of a rate-response algorithm represents the minimum signal amplitude from the sensor that is required to initiate a increase in pacing rate. Signals below this level will be ignored and under these conditions the pacemaker will continue at its predetermined minimum rate. A practical method in accordance with the embodiment of the invention for selecting an appropriate threshold level for individual patients is to measure the range of variation in amplitude of the incoming sensor signal under resting conditions. Once obtained, this measurement is stored as the threshold value for initiating a rate-response.

The first step in programming the rate-response algorithm of the illustrative embodiment is activation of "Threshold Selection" mode by means of a telemetered instruction from an external programmer.

While "Threshold Selection" is being performed, the patient is kept under resting conditions. The stage last s for some minutes to ensure that an adequate sample of resting signals has been monitored. Programmed deactivation of "Threshold Selection" mod causes the maximum sensor signal measured during this period to be electrically stored within the pacemaker for use by the rate-response algorithm. The stored value may be used as it stands, but it can also be subjected to predetermined increments or decrements to conform to the functional requirements of any different biological sensor system to which it is applied.

Adjusting Slope

It is possible to calculate appropriate "target heart rates" for a rate-response algorithm to achieve under a wide variety of conditions because (1) Any given form of normal daily exercise (such as walking or climbing stairs) will elicit approximately the same heart rate response in the majority of normal individual subjects.

(2) If an individual subject undertakes progressively increasing levels of exertion (such as a treadmill exercise) then there is an approximately linear relationship between the level of exertion and the increase in heart rate that occurs.

Once the value of the slope required to achieve a suitable heart rate for any given level of exertion has been duly selected, physiologically appropriate rates will be generated at all different exercise levels.

Slope selection circuitry in the illustrative embodiment of the pacemaker automatically varies the slope between preset minimum and maximum limits. The external programmer will be used to give the rate-response algorithm a "Target Rate" that is appropriate to a given level of exertion and at the same time to activate the "Slope Selection" mode The patient then commences the form of exercise chosen for him and after a fixed delay of say two minutes (to allow for physiological equilibration) the incline of the slope is progressively increased from its minimum value to a level at which the pacemaker's rate coincides with the "Target Rate". Once this has occurred "Slope Selection" mode automatically ceases and the value of the slope selected is stored for use in the rate-response algorithm.

By simplifying and automating the setting of the variables for the rate-response algorithm rapidly in each individual implantee this system offers improvements in both functional and economic terms. Furthermore, the likelihood of any operator error occurring may be reduced.

Figure 2:
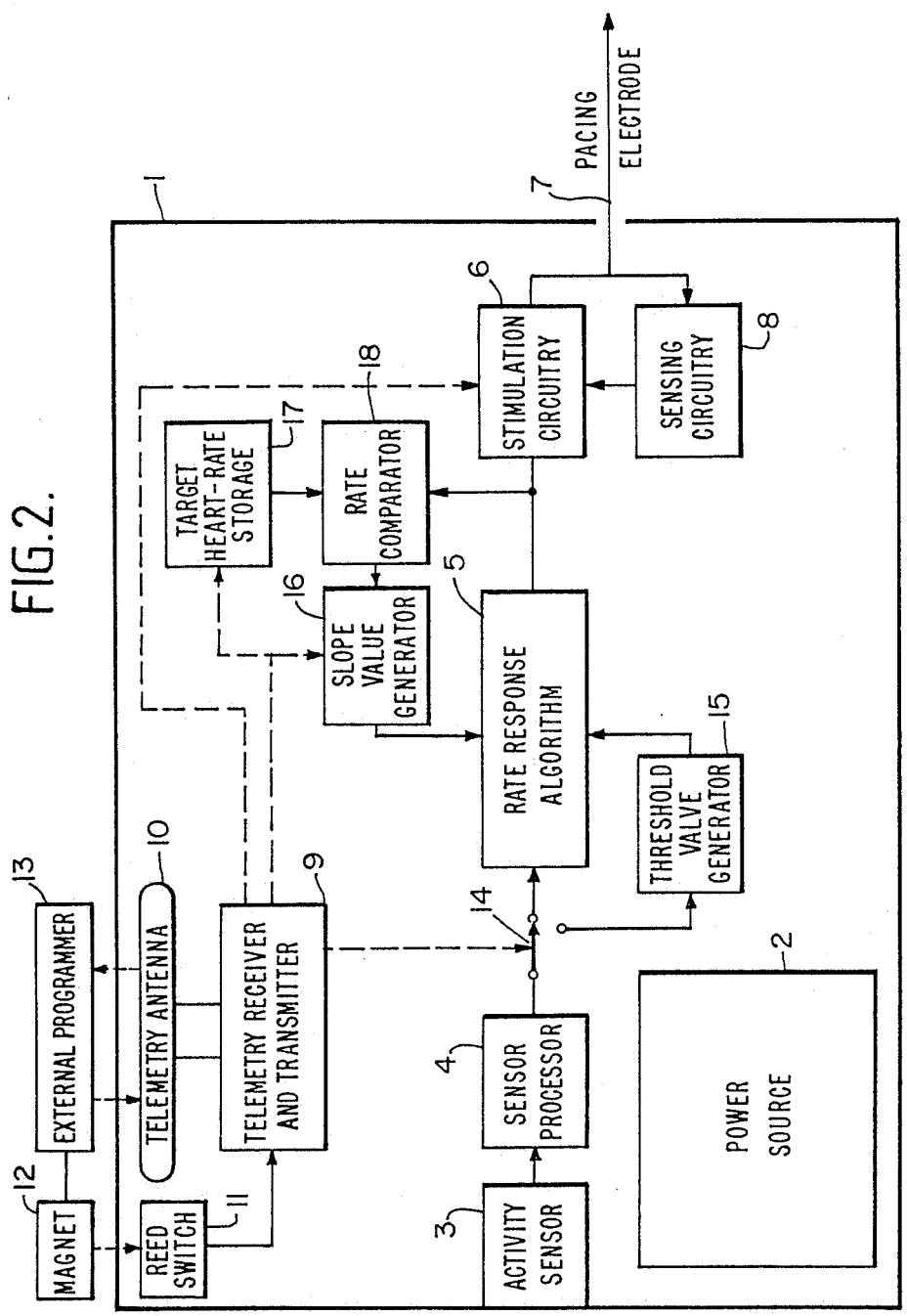

For a better understanding of the present invention, and to show how the same may be carried into effect, reference will now be made by way of example to the accompanying drawings, in which, FIG. 1 is a graph illustrating the form of a rate-response algorithm, and FIG. 2 is a schematic block diagram of an illustrative rate-responsive pacemaker according to the present invention.

The illustrative implantable rate-responsive pacemaker shown in FIG. 2 comprises a hermetically sealed can 1 containing a power source 2 (e.g. a battery), an activity sensor 3, a sensor processor 4, circuitry 5 defining a rate-response algorithm, and stimulating circuitry 6. A lead 7 extends from the stimulating circuitry 6 through the wall of the can to a pacing electrode (not shown) for applying an electrical stimulus to the heart of the user of the pacemaker. For simiplicity, the connections from the power source to the various circuits ar not illustrated.

Normal operation of the pacemaker will firstly be described For the purposes of this illustrative description, it is assumed that the sensor 3 senses body vibration although the principles of the present invention can be applied using all forms of biological sensor not just a body vibration sensor.

The activity sensor 3 detects body vibration to produce an activity signal representing the level of exertion of the user. The activity signal is amplified and processed by processor 4 to make the signal more suitable for processing in the circuitry 5.

The circuitry 5 implements the rate-response algorithm; that is the function relating the level of exertion represented by the activity signals to the pacing rate (R) of the pacemaker. As shown in FIG. 1, the algorithm defines a constant pacing rate until the amplitude of the processed activity signal S has a threshold level. The pacing rate R then varies according to a mathematical relationship (e.g. linearly) with the amplitude of the processed activity signal with a slope dR/dS. The pacing rate R has a programmable maximum value (which is not indicated on the graph).

The output of the circuitry 5 is a rate signal representing the pacing rate R appropriate to the user's level of exertion represented by the activity signal S. Stimulation circuitry 6 responds to the rate signal to provide an electrical stimulation to the user's heart via the pacing electrode 7. The lead 7 is a standard unipolar or bipolar transvenous pacing lead. Sensing circuitry 8 is employed to monitor the user's intrinsic cardiac behaviour. If the user's heart beats spontaneously at a rate higher than the pacing rate R, the output of pacemaker stimulation circuitry 6 will be inhibited. The pacemaker will thus function on demand in that it will only stimulate the user's heart to beat if the inherent natural heartrate falls below the physiologically appropriate rate R.

The activity sensor is shown in FIG. 2 within the can 1. It may be outside the can, being linked thereto via a lead. The sensor may be responsive to stimuli other than body vibration. Examples, as known, include body movement, respiratory rate, evoked QT interval, mixed venous oxygen saturation, right ventricular pressure and/or dimensions, and pH.

In accordance with one aspect of the invention, the threshold value and the slope of the rate-response algorithm are automatically adjustable when the pacemaker is set into a programming mode. In order to set the pacemaker in the programming mode and to provide programming information to the pacemaker, there is provided in the can 1 a telemetry receiver and transmitter 9, a telemetry antenna 10, and a reed switch 11 The receiver and transmitter 9 is inoperative until the reed switch 11 is actuated by an external magnet 12 Once made operative, the receiver 9 can respond to instructions and information transmitted thereto by an external programmer 13 (without use of a physical connection between the receiver and programmer). The transmitter and receiver are for example linked by radio frequency telemetry.

In order to set the threshold value, the programmer 13 causes the receiver 9 to activate switch 14 so that the output of the sensor processor 4 from the circuitry 5 is supplied to a threshold value generator 15. The generator 15 measures the peak amplitude of the processed signal over the period in which the pacemaker is in the "Threshold Select" mode. The peak value is stored in the generator for use either as itstands or in modified form as the threshold value for the algorithm. The modification may be a decrement or increment of the peak value. When the threshold select mode is deselected by the programmer, the switch 14 reconnects circuitry 5 to the processor 4 Whenever the pacemaker is functioning in threshold select mode stimulation circuitry 6 will remain active, providing a pacing stimulus on demand at the programmed minimum rate.

During the Threshold Select mode the user of the pacemaker is kept in a resting condition for several minutes to ensure that the threshold generator 15 samples the rest level activity signal S for an adequate time. The threshold level is thus determined by the actual rest level activity signal produced by the user.

In order to set the slope dR/dS, the programmer 13 causes the receiver 9 to actuate a slope value generator 16, which is initially set to a predetermined initial value of slope. That value could be a minimum value e.g. zero. The programmer also transmits a target value of pacing rate R which is stored in a store 17 The target value is a predetermined value of pacing rate chosen as appropriate to a particular level of exertion of the user.

The user performs the chosen level of exertion. The rate signal representing the pacing rate R produced in response to the resultant activity signal S is compared in a comparator 18 with the target rate in store 17. The value of slope generated by the generator 16 is adjusted until the actual pacing rate equals the target rate.

Upon achievement of equality, the value of slope is stored in generator 16. The adjustment of slope then ends, preferably automatically. The stored value of slope then controls the rate-response algorithm in normal operation of the pacemaker.

The stimulation 6 and sensing 8 circuitry is also capable of being programmed by the external programmer The circuitry 6, 8 is capable of functioning independently of the circuitry 5 to provide a constant demand pacing rate determined by the programmer. One or more of the functional parameters of the circuitry 6, 8 are variable by use of the programmer 13 over a preset range of values.

Those parameters include pulse amplitude and duration, sensitivity, and refractory period.

In a preferred embodiment of the invention the programmer 13 and pacemaker are operable to control the following modes of operation and parameters:

(a) Mode "Constant Rate", "Rate Response", "Threshold Select" and "Slope Select"

(b) Minimum pacing rate for "Constant Rate" or "Rate Response" modes.

(c) Maximum pacing rate - for "Rate Response" mode only.

(d) "Target Heart Rate" - any chosen value between (b) and (c) above.

(e) Pacemaker stimulation and sensing parameters (f) Telemetry function - to enable the pacemaker to transmit the values of all programmable parameters out to the external programmer.

Although the principles of automatic slope and threshold selection can be applied to all forms of sensor-modulated rate-responsive pacemakers, the technical details will require a degree of modification in order to conform to the functional requirements of different types of sensor. Thus in the case of respiratory sensing pacemakers, the function of the threshold value generator will be to measure the amplitude of the changes in chest wall impedance that are detected under resting conditions Once this value has been determined, it will be decremented by a preset amount before being stored for subsequent use as the threshold for the rate response algorithm.

Modifications of this sort will be required for each different type of sensor. More extensive changes will be required if the automatic circuitry is incorporated into complex second generation pacing systems with two or more simultaneous sensor inputs, but the same fundamental principles will still apply.

Although an embodiment of the invention has been illustratively described as allowing automatic adjustment of two parameters e.g. slope and threshold other embodiments could allow automatic adjustment of only one parameter, e.g. slope or threshold

We claim:

1. A pacemaker comprising:

means for producing a first signal indicative of a sensed level of activity of a user, means responsive to said first signal for producing a second signal as a predetermined function of the first signal to control pacing rate, and selectively operable means for, when the pacemaker is put in a programming mode, adjusting said function, and comprising:

means for storing a given signal indicative of a particular value of said second signal corresponding to a predetermined level of exercise performed by said user, and means for varying said function until said second signal is equal to said given signal in response to the first signal produced while the user is performing said predetermined level of exercise.

2. A pacemaker according to claim 1, wherein said varying means is operable, in said programming mode of said pacemaker, for effecting said variation of said function automatically until said second signal assumes said particular value.

3. A pacemaker according to claim 1, wherein said function is linear over a range of values of said first signal, and said varying means effects the varying of said function by varying the slope of said linear function.

4. A pacemaker according to claim 2 or 3, including telemetering receiving means for receiving said signal to be stored in said storing means.

5. A pacemaker according to claim 1, including telemetering receiving means for receiving said signal to be stored in said storing means.

6. A pacemaker according to claim 2, 3, or 5, wherein said function adjusting means adjusts said function so that said pacing rate is not increased above a resting level until said first signal exceeds a threshold.

7. A pacemaker according to claim 1, wherein said function adjusting means adjusts said function so that said pacing rate is not increased above a resting level until said first signal exceeds a threshold.

8. A pacemaker according to claim 7, wherein said function adjusting means includes means for, when the pacemaker is put in said programming mode, setting said threshold, said threshold setting means being operable for sensing variations in said first signal while the user is resting and for selecting the threshold dependent upon said variations.

9. A pacemaker according to claim 8, wherein said threshold setting means is operable to store a peak value of said first signal which occurs during variations thereof while the user is resting and for setting said threshold based on said stored peak value.

10. A pacemaker according to any of claims 1 to 9, wherein said means for producing said first signal comprises a sensor for sensing evokedQt interval.

11. A pacemaker according to any of claims 1 to 9, wherein said means for producing said first signal comprises a sensor for sensing respiratory rate.

12. A pacemaker according to any of claims 1 to 9, wherein said means for producing said first signal comprises a sensor for sensing mixed venous temperature.

13. A pacemaker according to any of claims 1 to 9, wherein said means for producing said first signal comprises a sensor for sensing bodily vibration.

14. A pacemaker comprising:

means for producing a first signal indicative of a sensed level of activity of a user, means for producing a second signal to control pacing rate and being related to said first signal by a predetermined function such that said second signal changes only in response to said first signal exceeding a threshold, and selectively operable means for, when the pacemaker is put in a programming mode, varying said threshold, said threshold varying means being operable for sensing variations in said first signal while the user is resting and for selecting the threshold based on said variations.

15. A method of adjusting a rate responsive pacemaker to cause the pacing rate thereof to assume a value required by a user of the pacemaker to perform at a particular level of exertion, the method comprising the steps of:

producing an activity signal representing the level of exertion of the user;

controlling pacing rate to be a predetermined function of said activity signal, said function including a slope component, producing a first activity signal representing a rest level of exertion of the user, in a programming mode:

for said activity signal, setting a threshold level based on said first activity signal representing the rest level of exertion so that at said threshold level a transition occurs in the output of said function between a constant pacing rate and a pacing rate which varies with the level of the activity signal, providing a signal representative of a predetermined value of pacing rate corresponding to a predetermined level of exertion by said user, other than the rest level, producing a second activity signal representing the said predetermined level of exertion of the user, and adjusting the slope of said function until the second activity signal representing the said predetermined level of exertion produces via said function a pacing rate representative signal that equals the pacing rate signal representative of the predetermined value of pacing rate.

* * * * *